(12) United States Patent
Oren et al.

(10) Patent No.: US 6,511,487 B1
(45) Date of Patent: Jan. 28, 2003

(54) SUTURING INSTRUMENT AND METHOD

(75) Inventors: Ran Oren, Doar Na Oshrat (IL); Dan Moor, Doar Na Oshrat (IL)

(73) Assignee: T. A. G. Medical Products Ltd., Kibbutz Gaaton (IL)

( * ) Notice: Subject to any disclaimer, the term of this patent is extended or adjusted under 35 U.S.C. 154(b) by 72 days.

(21) Appl. No.: 09/722,712

(22) Filed: Nov. 28, 2000

(51) Int. Cl.[7] .............................................. A61B 17/04
(52) U.S. Cl. ..................................................... 606/145
(58) Field of Search .......................... 606/145; 112/169, 112/116, 199, 194

(56) References Cited

U.S. PATENT DOCUMENTS 5,843,099 A * 12/1998 Nichols et al. ............. 606/144

* cited by examiner

Primary Examiner—John J. Calvert
Assistant Examiner—James G Smith
(74) Attorney, Agent, or Firm—G. E. Ehrlich Ltd.

(57) ABSTRACT

A suturing instrument includes a jaw and a pivotally mounted puncturer to be located on opposite sides of the tissue to be sutured. The suture is applied while the puncturer is in an open position on one side of the jaw, and the needle is then pivoted to a closed position through an opening in the jaw to pierce the tissue and to bring a portion of the suture to the opposite side of the jaw. At the opposite side of the jaw, a crochet head is actuated to engage the suture and to clamp it to the jaw as the puncturer is pivoted back to its open position.

20 Claims, 2 Drawing Sheets

SUTURING INSTRUMENT AND METHOD

FIELD AND BACKGROUND OF THE INVENTION

The present invention relates to a suturing instrument useful in surgery, and also to a method of applying a suture to tissue during surgery.

Many surgical procedures are presently being performed via an endoscope in order to minimize the size of the incisions and the trauma to the patient. In such procedures, the surgical instrument is generally introduced through a cannula or passageway in the endoscope while the surgeon views the surgical site through another passageway in the endoscope. A number of forceps-type suturing instruments have been designed for introduction through a cannula used in endoscope procedures is a forceps-type suturing instrument, such as disclosed in U.S. Pat. No. 5,730,747 and 6,051,006. The known suturing instruments of this type, however, are generally of relatively complicated construction and/or are useful only with respect to needled sutures.

OBJECTS AND SUMMARY OF THE INVENTION

An object of the present invention is to provide a suturing instrument of relatively simple construction and which can be used with unneedled sutures, i.e., suture threads per se, i.e., without a puncturer being attached to the suture. Another object of the invention is to provide a suturing instrument particularly useful as a forceps type instruments for introduction through a cannula used in endoscopic procedures. A further object of the invention is to provide a novel method of applying a suture to tissue.

According to one aspect of the present invention, there is provided a suturing instrument, comprising: a jaw formed with an opening therethrough; a puncturer pivotally mounted from an open position on one side of the jaw to a closed position through the opening to the opposite side of the jaw, the puncturer being constructed to receive a suture in the open position of the puncturer and to move a portion of the suture through the jaw opening to the opposite side f the jaw when actuated to the closed position of the puncturer; and a crochet head for engaging the portion of the suture at the opposite side of the jaw opening and for clamping the suture to the jaw thereby permitting the puncturer to return to its open position while disengaged from the suture.

According to further features in the preferred embodiment of the invention described below, the crochet head is slidably mounted at the opposite side of the jaw and is movable through a forward stroke from a retracted position at the proximal end of the jaw to an extended position at the distal end of the jaw, and through a return stroke back to the retracted position. The crochet head has a shaped surface effective to engage the portion of the suture at the opposite side of the jaw during the forward stroke of the crochet head, and to clamp same to the jaw during the return stroke of the crochet head.

According to still further features in the described preferred embodiment, the jaw is part of a frame assembly including a proximal section formed with a first handle, and a distal section carrying the jaw; and the puncturer is part of a puncturer assembly including a proximal section formed with a second handle pivotally mounted with respect to the first handle, a distal section including the pivotally mounted puncturer, and a coupling between the second handle and puncturer for pivoting the puncturer from the open position to the closed position upon pivoting the second handle with respect to the first handle. Similarly, the crochet head is part of a crochet head assembly including a proximal section formed with a third handle pivotally mounted with respect to the first handle, a distal section carrying the crochet head, and a coupling for moving the crochet head through its forward and return strokes by the pivoting of the third handle with respect to the first handle.

As will be described more particularly below, the foregoing features enable suturing instruments to be constructed with a relatively few simple parts and to be used unneedled sutures.

According to another aspect of the present invention, there is provided a method of applying a suture to tissue, comprising: pivotally mounting a puncturer with respect to a jaw having an opening therethrough such that the puncturer is pivotal from an open position on one side of the jaw through the opening in the jaw to a closed position on the opposite side of the jaw; applying a suture to the puncturer when the puncturer is in its open position on one side of the jaw; locating the jaw on one side and the pivotal puncturer on the opposite side, of the tissue to be sutured; pivoting the puncturer towards the jaw to pierce the tissue and to pass the puncturer therethrough and through the opening in the jaw to the closed position of the puncturer on the opposite side of the jaw, and thereby to bring a portion of the suture with the puncturer to the opposite side of the jaw; clamping to the jaw the portion of the suture at the opposite side of the jaw; and pivoting the puncturer back to its open position while the suture is clamped to the jaw.

Further features and advantages of the invention will be apparent from the description below.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to shown structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
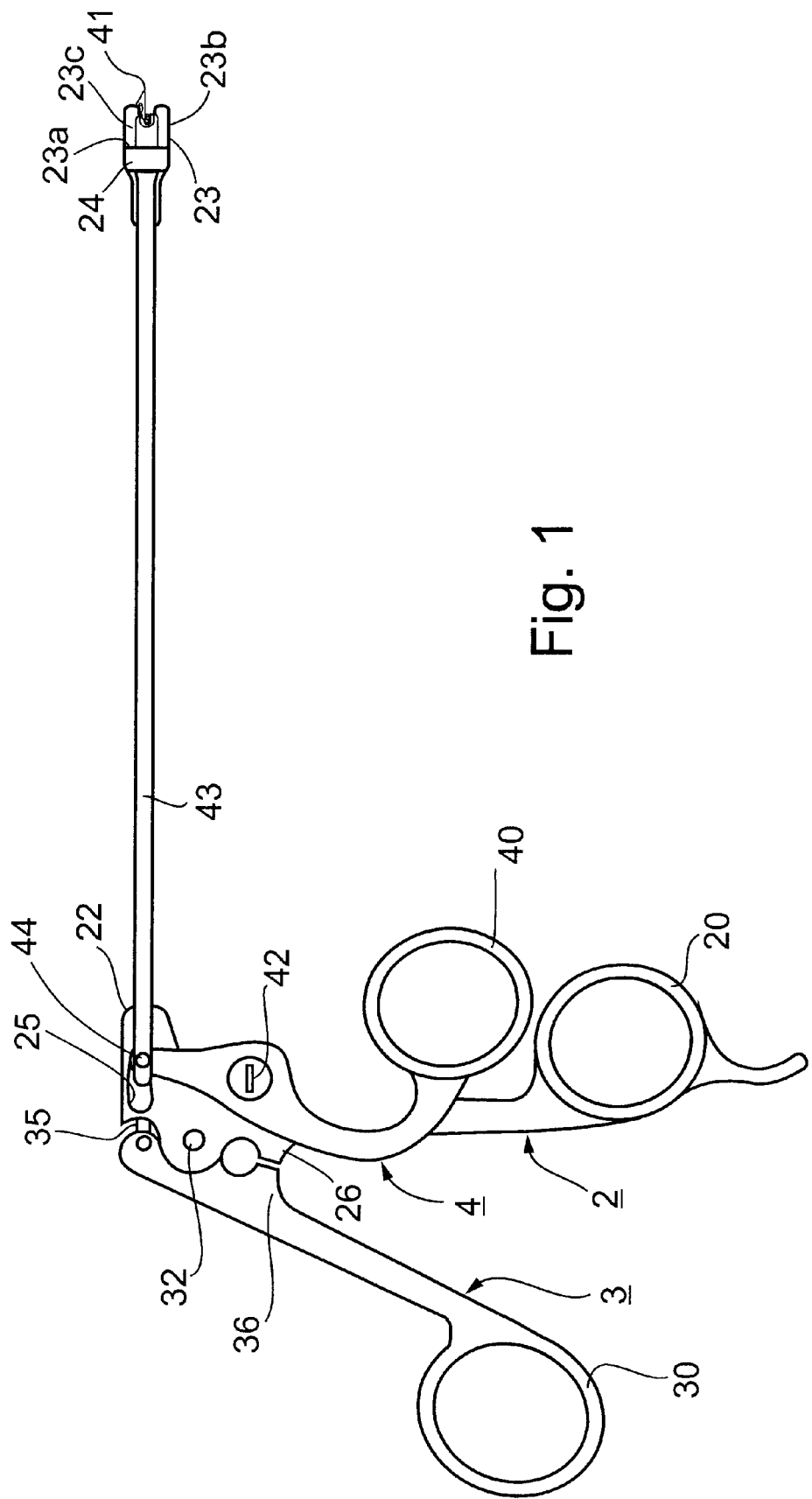
FIG. 1 is a side view illustrating one form of suturing instrument constructed in accordance with the present invention.

The present invention is of a suturing device and method which can be used to efficiently insert a suture in tissue during surgery. Specifically, the present invention can be used in minimally invasive, endoscope, laparoscope or athroscope assisted surgeries.

The principles and operation of a device and method according to the present invention may be better understanding with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The suturing instrument illustrated in FIG. 1 is of the forceps type particularly useful by applying it through a cannula used in endoscopic procedures in order to suture tissue at the surgical site.

Figure 2:
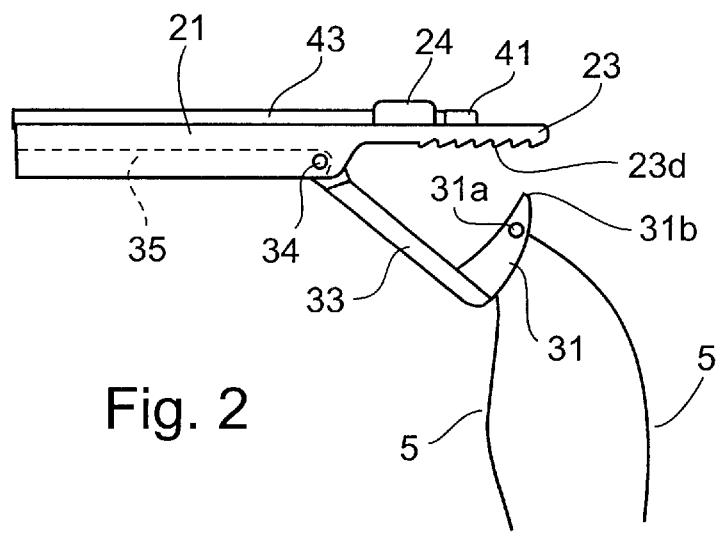
FIG. 2 is an enlarged bottom view of the distal end of the suturing instrument illustrating the puncturer in its open position for receiving a suture.

The illustrated suturing instrument is constituted of three main assemblies:

(1) a frame assembly, generally designated 2, including a first handle 20 at one end (hereinafter called the proximal end), fixed substantially perpendicularly to an elongated shank 21 (FIG. 2);

(2) a puncturer assembly, generally designated 3, including a second handle 30 at the proximal end of the instrument, pivotally mounted to the frame assembly 2 and coupled to a puncturer 31 (FIG. 2) pivotally mounted at the distal end of the elongated shank 21; and (3) a crochet head assembly, generally designated 4, including a third handle 40 also pivotally mounted to the frame assembly 2 and coupled to a slidable crochet head 41 at the distal end of the elongated shank 21.

As will be described more particularly below, the suture, shown at 5 in FIG. 2, is loaded onto the puncturer 31 when in its open position as illustrated in FIG. 2.

With respect to the frame assembly 2, the proximal end of the elongated shank 21 is fixed within a perpendicular extension 22 at the upper end of handle 20. The distal end of the elongated shank 21 carries a fixed jaw 23 formed with a pair of legs 23a, 23b parallel to the axis of the elongated shank 21 and spaced from each other to define a space 23c. As shown particularly in FIG. 2, the inner surface of jaw 23 facing the pivotal puncturer 31 is ribbed as shown at 23d in order to firmly grasp the tissue to be sutured between it and the pivotal puncturer, as will be described below.

The distal end of the elongated shank 21 further includes a U-shaped member 24 serving as a guide for a part of the crochet head assembly 4, as will be described below. In addition, extension 22 of handle 20 is formed with a slot 25 (FIG. 1) at the proximal end of the elongated shank 21, for accommodating a coupling element of the crochet head assembly 4 as will also be described below. Further, the upper end of handle 20 of the frame assembly 2 includes an abutment 26 serving as a stop for limiting the pivotal movement of handle 30 of the puncturer assembly 3.

With respect to the puncturer assembly 3, handle 30 of that assembly is pivotally mounted at 32 to the upper end of handle 20 of the frame assembly 2. As shown particularly in FIG. 2, puncturer 31 pivotally mounted at the distal end of the elongated shank 21, is formed with a hole 31a for receiving the suture 5, and with a pointed tip 31b for piercing the tissue clamped between it and the ribbed surface 23d of the fixed jaw 23.

Puncturer 31 is pivotally mounted to the distal end of the elongated shank 21 by an arm 33 carrying the puncturer 31 at one end, and pivotally mounted at its opposite end 34 to the elongated shank 21. Arm 33 is coupled to the upper end of handle 30 of the puncturer assembly 3 by a rod 35 (FIG. 1) passing through, or alongside of, the elongated shank 21. The arrangement is such that pivoting handle 30 away from handle 20 pivots puncturer 31 to its open position illustrated in FIG. 2 for receiving the suture 5, and pivoting handle 30 towards handle 20 moves puncturer 31 through the opening 23c in the jaw 23 to pierce the tissue clamped between the puncturer and the jaw, and to bring the suture 5 to the opposite side of the jaw. Handle 30 is formed on its inner face with an abutment 36 engagable with abutment 26 of handle 20 to limit the latter pivotal movement of handle 30.

With respect to the crochet head assembly 4, its handle 40 is pivotally mounted at 42 to the upper end of handle 20 of the frame assembly 2. Preferably, this pivotal mounting includes a piano spring (not shown) to bias the handle 40 to the position illustrated in FIG. 1, which is the retracted position of the crochet head 41.

The crochet head 41 is carried at the distal end of a slide 43 extending along one side of the elongated shank 21. The proximal end of slide 43 is coupled by a pin 44 (FIG. 1) to the upper end of handle 40. Pin 44 is movable within slot 25 in the extension 22 at the upper end of handle 20 to limit the pivotal movements of handle 40 with respect to handle 20. As will be described below, handle 40 may be pivoted with respect to handle 20 to move slide 43, and the crochet 41 carried at the distal end of the slide, through forward and return strokes parallel to the longitudinal axis of the elongated shank 21. The forward and return movements of the slide 43 are guided by the U-shaped member 24 at the distal end of the elongated shank.

Figure 3:
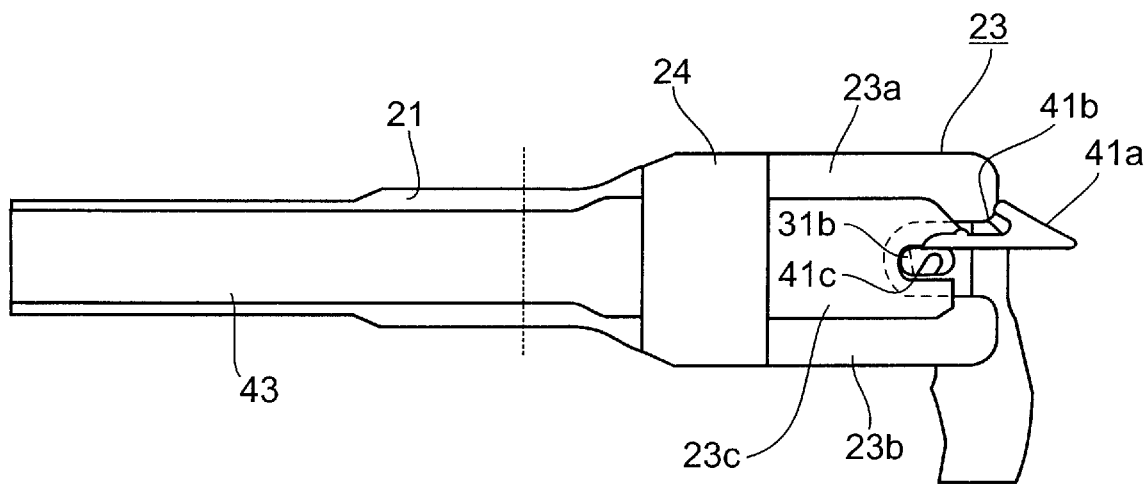
FIG. 3 is an enlarged side view of the distal end of the suturing instrument of FIG. 1 with the crochet head in its extended position.

The structure of the crochet head 41 is more particularly illustrated in FIG. 3. It includes a tapered nose 41a at one end for engaging the suture 5 during the forward movement of the crochet head, and a hook formation at the opposite end for receiving the suture and for clamping it to the jaw 23 during the return movement of the crochet head. The crochet head is further formed with an axial slot 41c to accommodate the pointed tip 31b of the puncturer 31 when the puncturer is pivoted to its closed position and the crochet has been moved to its most forward position.

The illustrated suturing instrument may be used in the following manner.

First, handle 30 is provided away from handle 20 so as to pivot the puncturer 31 to its open position as shown in FIG. 2, to enable the suture 5 to be loaded thereon by passing the suture through opening 31a of the puncturer.

Handle 30 may then be pivoted towards handle 20 to move the puncturer 31, together with the portion of the suture carried thereby, to the closed position of the puncturer, i.e., through opening 23c of jaw 23. This enables the distal portion of the instrument to be inserted through the cannula (not shown) of the endoscope. After the distal portion of the instrument has passed through the cannula and is located in the surgical site, handle 30 may be pivoted away from handle 20 to return the puncturer to its open position, as shown in FIG. 2, preparatory to its use for suturing tissue. In this condition of the instrument, handle 40 is in the position shown in FIG. 1, such that the crochet head 41 actuated by the handle is in its retracted position on the proximal side of jaw 23.

The surgeon may then manipulate the instrument with the puncturer 31 in its open position to locate the puncturer on one side of the tissue to be sutured, and to locate the jaw 23 on the opposite side of the tissue to be sutured. The surgeon then moves handle 30 towards handle 20, which thereby, by virtue of the coupling rod 35, pivots puncturer 31 towards jaw 23 and then through the opening 23c in the jaw, to thereby pierce the tissue and to bring the portion of suture 5 within the needle hole 31a to the opposite side of the jaw. While the puncturer is in its closed position, handle 40 is then pivoted clockwise to move the crochet head 41, coupled to the handle by slide 43, through a forward stroke parallel to the elongated shank 21 from the proximal side of the jaw 23 to the distal side thereof, and then releases handle 40 to permit its spring bias to return the crochet head through a return stroke back to its initial position at the proximal side of the jaw.

During the movement of the crochet head in the forward stroke, its nose 41a engages the suture that has been passed through opening 23c in jaw 23, and guides the suture to the block portion 41b of the crochet head, such that when the crochet head returns during the return stroke back to its initial position, the hook portion 41b of the crochet head clamps the suture to the jaw 23. Handle 30 may then be moved away from handle 20 to pivot the puncturer 31 to its open position, and thereby to release the tissue. The instrument may then be used for applying another suture to another portion of the tissue by repeating the foregoing steps.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that may alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A suturing instrument, comprising:
   (a) a jaw formed with an opening therethrough;
   (b) a puncturer pivotally mounted from an open position on one side of the jaw to a closed position through said opening on the opposite side of the jaw, said puncturer being constructed to receive a suture in the open position of the puncturer and to move a portion of the suture through said jaw opening to the opposite side of the jaw when actuated to the closed position of the puncturer; and
   (c) a crochet head for engaging the portion of the suture at said opposite side of the jaw opening and for clamping the suture to the jaw, thereby permitting the puncturer to return to its open position while disengaged from the suture.

2. The instrument according to claim 1, wherein:
   said jaw includes a proximal end and a distal end;
   said crochet head is slidably mounted at said opposite side of the jaw and is movable through a forward stoke from a retracted position at the proximal end of the jaw to an extended position at the distal end of the jaw, and through a return stroke back to said retracted position; and
   said crochet head has a shaped surface effective to engage the portion of the suture at said opposite side of the jaw during the forward stroke of the crochet had, and to clamp same to the jaw during the return stroke of the crochet head.

3. The instrument according to claim 2, wherein said puncturer is formed with a hole for receiving said suture.

4. The instrument according to claim 1, wherein:
   said jaw is part of a frame assembly including a proximal section formed with a first handle, and a distal section carrying said jaw; and
   said puncturer is part of a puncturer assembly including a proximal section formed with a second handle pivotally mounted with respect to said first handle, a distal section including said pivotally mounted puncturer, and a coupling between said second handle and puncturer for pivoting said puncturer from said open position to said closed position upon pivoting the second handle with respect to the first handle.

5. The instrument according to claim 4, wherein said crochet head is part of a crochet assembly including a proximal section formed with a third handle pivotally mounted with respect to said first handle, a distal section carrying said crochet head, and a coupling for moving said crochet head through its forward and return strokes by the pivoting of said third handle with respect to said first handle.

6. The instrument according to claim 5, wherein said third handle is spring-biased to its retracted position.

7. The instrument according to claim 5, wherein:
   said frame assembly includes an elongated shank between said first handle and said jaw; and
   said coupling of the crochet head assembly includes a slide slidable with respect to said elongated shank and carrying said crochet head at the distal end of the slide.

8. The instrument according to claim 7, wherein:
   said coupling of the puncturer assembly includes a rod extending through said elongated shank of the frame assembly; and
   said slide of the crochet head assembly extends along one side of said elongated shank of the frame assembly.

9. The instrument according to claim 7, wherein said elongated shank of the frame assembly includes a U-shaped guide member at the distal end of the shank adjacent to said jaw and enclosing said slide of the crochet head assembly for guiding the forward and return movements of the crochet head.

10. The instrument according to claim 7, wherein said first handle of the frame assembly is fixed substantially perpendicularly to said elongated shank of the frame assembly.

11. The instrument according to claim 7, wherein said second handle of the puncturer assembly is pivotally mounted to said first handle of the frame assembly adjacent to said elongated shank.

12. The instrument according to claim 7, wherein said jaw of the frame assembly is formed with two legs parallel to said elongated shank and spaced from each other to define a space for receiving the puncturer in the closed position of the puncturer.

13. The instrument according to claim 7, wherein said puncturer is pivotally mounted to the elongated shank of the frame assembly adjacent to said jaw.

14. The instrument according to claim 7, wherein the face of said jaw facing the puncturer in the open position of the puncturer is formed with a ribbed surface to firmly clamp tissues pierced by the puncturer when the puncturer is provided to its closed position through said opening in the jaw.

15. The instrument according to claim 7, wherein said frame assembly is formed with a slot, and said slide of the crochet head assembly is coupled at its proximal end to said third handle by a pin movable in said slot and engagable with the ends of the slot to limit the forward and return movements of the slide and of the crochet head carried thereby.

16. The instrument according to claim 7, wherein said crochet head includes a tapered nose at one end for engaging the suture during the forward movement of the crochet head, and a hook formation at the opposite end for receiving the suture and for clamping same to the jaw during the return movement of the crochet head.

17. A method of applying a suture to tissue, comprising the steps of:
 (a) pivotally mounting a puncturer with respect to a jaw having an opening therethrough such that the puncturer is pivotal from a open position on one side of the jaw through said opening in the jaw to a closed position on the opposite side of the jaw;
 (b) applying a suture to the puncturer when the puncturer is in its open position on one side of the jaw;
 (c) locating the jaw and the pivotal puncturer on opposite sides of the tissue to be sutured;
 (d) pivoting the puncturer towards the jaw to pierce said tissue and to pass the puncturer therethrough and through said opening in the jaw to the closed position of the puncturer on the opposite side of the jaw, and thereby to bring a portion of the suture with the puncturer to the opposite side of the jaw;
 (e) clamping to the jaw the portion of the suture at said opposite side of the jaw; and
 (f) pivoting the puncturer back to its open position while the suture is clamped to the jaw.

18. The method according to claim 17, wherein the portion of the suture on said opposite side of the jaw is clamped to the jaw by moving a crochet head from a retracted position to an extended position and back to its retracted position after the puncturer has been pivoted to its closed position and before the puncturer is pivoted back to its open position.

19. The method according to claim 18, wherein the puncturer is formed with a hole for receiving the suture in the open position of the puncturer.

20. The method according to claim 18, wherein said crochet head includes a tapered nose at one end for engaging the suture during the forward movement of the crochet head, and a hook formation at the opposite end for receiving the suture and for clamping same to the jaw during the return movement of the crochet head.

* * * * *

UNITED STATES PATENT AND TRADEMARK OFFICE
CERTIFICATE OF CORRECTION

PATENT NO.     : 6,511,487 B1                                              Page 1 of 1
DATED          : January 28, 2003
INVENTOR(S)    : Oren et al.

It is certified that error appears in the above-identified patent and that said Letters Patent is hereby corrected as shown below:

<u>Column 6,</u>
Line 7, change "had" to -- head --.

<u>Column 7,</u>
Line 3, change "provided" to -- pivotted --.

Signed and Sealed this

Third Day of June, 2003

JAMES E. ROGAN
*Director of the United States Patent and Trademark Office*